United States Patent [19]

Porter et al.

[11] Patent Number: 5,612,331
[45] Date of Patent: Mar. 18, 1997

[54] TETRAHYDROCARBAZOLE DERIVATIVES AS 5-HT1-LIKE AGONISTS

[75] Inventors: Roderick A. Porter, Hertfordshire; Mythily Vimal, London, both of England

[73] Assignee: SmithKline Beecham PLC, United Kingdom

[21] Appl. No.: 464,615

[22] PCT Filed: Dec. 16, 1993

[86] PCT No.: PCT/EP93/03628

§ 371 Date: Jul. 26, 1995

§ 102(e) Date: Jul. 26, 1995

[87] PCT Pub. No.: WO94/14773

PCT Pub. Date: Jul. 7, 1994

[30] Foreign Application Priority Data

Dec. 21, 1992 [GB] United Kingdom ............... 9226566

[51] Int. Cl.$^6$ .................... A61K 31/40; C07D 209/88
[52] U.S. Cl. ................. 514/212; 514/323; 514/411; 540/602; 546/200; 548/448
[58] Field of Search ............ 548/448; 546/200; 540/602; 514/212, 323, 411

[56] References Cited

U.S. PATENT DOCUMENTS 4,257,952  3/1981  Mooradian ............... 564/439

FOREIGN PATENT DOCUMENTS 2035310  6/1980  United Kingdom .
2191488  12/1987  United Kingdom .
WO-A-93/ 00086  1/1993  WIPO .

OTHER PUBLICATIONS

J. Med Chem, vol. 36, No. 13, Jun. 1993, pp. 1918–1919, F.D.King et al: '3–Amino–6–carboxamido–1,2,3,4–tetrahydrocarbazole: a conformationally restricted analogue of 5–carboxamidotryptamine with selectivity for the serotonin 5–HT1D receptor'.

*Primary Examiner*—Richard L. Raymond
*Attorney, Agent, or Firm*—Nora Stein-Fernandez; William T. King; Edward T. Lentz

[57] ABSTRACT

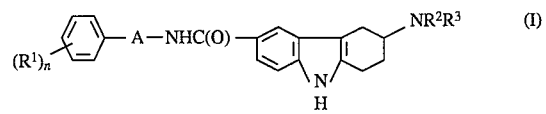

Compounds of formula (I), wherein $R^1$ represents halogen, $C_{1-4}$alkyl, $C_{1-4}$alkoxy, hydroxy, $NO_2$, $-NR^4R^5$, $R^4R^5NCO(CH_2)_m-$, $R^4R^5NSO_2(CH_2)_m-$, $R^6CONH(CH_2)-_m$ or $R^7SO_2NH(CH_2)_m-$; $R^4$ and $R^5$ each independently hydrogen or $C_{1-4}$alkyl or $NR?_4R^5$ represents a 5- to 7-membered heterocyclic ring, $R^6$ represents hydrogen or $C_{1-4}$alkyl; $R^7$ represents $C_{1-4}$alkyl; m is zero, 1 or 2; n is zero or 1 to 5; $R^2$ and $R^3$ each independently represent hydrogen, $C_{1-6}$alkyl or benzyl or $-NR^2R^3$ represents a pyrrolidino, piperidino or hexahydroazepino ring, and A represents a bond, a $C_{1-5}$alkylene chain or a $C_{3-5}$alkenyle chain wherein the double bond is not adjacent the nitrogen atom; and salts thereof have affinity for the 5-HT$_1$-like receptor and are useful e.g. in the treatment of migraine.

9 Claims, No Drawings

TETRAHYDROCARBAZOLE DERIVATIVES AS 5-HT1-LIKE AGONISTS

This application is a 371 of PCT/EP93/03628, filed Dec. 16, 1993.

The present invention relates to novel tetrahydrocarbazole derivatives, processes for preparing them, pharmaceutical compositions containing them and their use in therapy, in particular for the treatment of migraine.

U.S. Pat. Nos. 4,257,952, 4,172,834, 4,062,864 and 3,959,309 describe a broad class of 3-amino and 3-(substituted amino) tetrahydrocarbazoles having a variety of substituents at the 5,6,7 and/or 8 positions, including inter alia the group —CONR$_2$R$_3$ wherein R$_2$ and R$_3$ are hydrogen, lower alkyl or together with the nitrogen atom form a heterocyclic ring. Such compounds are said to have analgetic, psychotropic and antihistaminic properties.

International Application No WO 93/00086 describes 3-amino and 3-(substituted amino) tetrahydrocarbazoles substituted at the 6-position of the tetrahydrocarbazole ring by a substituent selected from hydrogen, halogen, trifluoromethyl, nitro, hydroxy, $C_{1-6}$alkyl, $C_{1-6}$alkoxy, aryl$C_{1-6}$alkoxy, —CO$_2$R$^4$, —(CH$_2$)$_n$CN, —(CH$_2$)$_n$CONR$^5$R$^6$, —(CH$_2$)$_n$SO$_2$NR$^5$R$^6$, $C_{1-6}$alkanoylamino(CH$_2$)$_n$, or $C_{1-6}$alkylsulphonylamino(CH$_2$)$_n$; and R$^5$ and R$^6$ represent hydrogen or $C_{1-6}$alkyl, or together with the nitrogen atom form a ring. The compounds are said to be 5-HT$_{1-like}$ agonists.

We have now found novel tetrahydrocarbazole derivatives having affinity for 5-HT$_1$-like receptors.

The present invention provides in a first aspect a compound of formula (I):

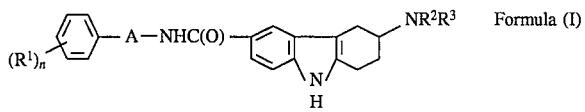

Formula (I)

wherein

R$^1$ represents halogen, $C_{1-4}$alkyl, $C_{1-4}$alkoxy, hydroxy, NO$_2$, —NR$^4$R$^5$, R$^4$R$^5$NCO(CH$_2$)$_m$—, R$^4$R$^5$NSO$_2$(CH$_2$)$_m$—, R$^6$CONH(CH$_2$)$_m$— or R$^7$SO$_2$NH(CH$_2$)$_m$—;

R$^4$ and R$^5$ each independently represent hydrogen or $C_{1-4}$alkyl or NR$^4$R$^5$ represents a 5- to 7-membered heterocyclic ring;

R$^6$ represents hydrogen or $C_{1-4}$alkyl;

R$^7$ represents $C_{1-4}$alkyl;

m is zero, 1 or 2;

n is zero or 1 to 5;

R$^2$ and R$^3$ each independently represent hydrogen, $C_{1-6}$alkyl or benzyl or —NR$^2$R$^3$ represents a pyrrolidino, piperidino or hexahydroazepino ring; and A represents a bond, a $C_{1-5}$alkylene chain or a $C_{3-5}$alkenylene chain wherein the double bond is not adjacent the nitrogen atom;

or a salt thereof.

In the compounds of formula (I) a halogen atom may be a fluorine, chlorine, bromine or iodine atom. An alkyl or alkylene group or moiety may have a straight or branched chain. A $C_{1-4}$alkyl group may be for example methyl, ethyl, n-propyl, n-butyl or any branched isomer thereof such as isopropyl, or t-butyl, and a $C_{5-6}$alkyl group may for example include n-pentyl, or n-hexyl or any branched isomer thereof such as sec-pentyl.

When —NR$^4$R$^5$ represents a heterocyclic ring this is preferably a 5- to 7-membered saturated heterocyclic ring which may optionally contain a further heteroatom selected from oxygen, sulphur or nitrogen. Suitable rings thus include pyrrolidino, piperidino, piperazino and morpholino. It will be appreciated that when the ring includes a further nitrogen atom this will carry a hydrogen atom or a suitable substituent group such as a $C_{1-4}$alkyl group.

The group A preferably represents a $C_{1-4}$alkylene chain or a $C_{3-4}$alkenylene chain. Most preferably A represents —(CH$_2$)$_2$—, —(CH$_2$)$_3$— or —CH=CHCH$_2$—.

n may be for example from zero to 3; preferably n is zero or 1.

R$^1$ preferably represents halogen e.g. bromo or chloro, $C_{1-4}$alkoxy e.g. methoxy, NO$_2$, —NR$^4$R$^5$, R$^4$R$^5$NSO$_2$(CH$_2$)$_m$—, or R$^7$SO$_2$NH(CH$_2$)$_m$— where R$^4$, R$^5$, R$^7$ and m are as defined above. Preferably R$^4$ and R$^5$ independently represent hydrogen or methyl. R$^7$ preferably represents methyl. m preferably represents zero.

Most preferably n is zero, or n is 1 and R$^1$ represents $C_{1-4}$alkoxy e.g. methoxy.

R$^2$ and R$^3$ each preferably represent hydrogen, methyl or ethyl. Most preferably NR$^2$R$^3$ is —NH$_2$.

It will be appreciated that for use in medicine a salt of formula (I) should be a physiologically acceptable salt. Suitable physiologically acceptable salts will be apparent to those skilled in the art and include for example acid addition salts such as those formed with inorganic acids e.g. hydrochloric, sulphuric or phosphoric acids and organic acids e.g. succinic, maleic, acetic or fumaric acid. Other non-physiologically acceptable salts e.g. oxalates may be used for example in the isolation of compounds of formula (I), and are included within the scope of this invention. Also included within the scope of the invention are solvates and hydrates of compounds of formula (I).

The compounds of formula (I) contain at least one asymmetric centre, viz, at the 3-position of the tetrahydrocarbazole ring, and may contain other centres of asymmetry, depending on the values of R$^1$, R$^2$ and R$^3$. Such compounds will exist as optical isomers (enantiomers) and the invention encompasses all such enantiomers and mixtures, including racemic mixtures, thereof. Compounds of formula (I) containing a double bond may exist as geometric isomers and all such isomers and mixtures thereof are included within the scope of this invention.

Particular compounds of the invention include:

3-amino-6-N-(3-phenylpropyl)carboxamido-1,2,3,4-tetrahydrocarbazole, 3-amino-6-N-(4-phenylbutyl)carboxamido-1,2,3,4-tetrahydrocarbazole, 3-amino-6-N-(2-phenylethyl)carboxamido-1,2,3,4-tetrahydrocarbazole, 3-amino-6-N-(benzylmethyl)carboxamido-1,2,3,4-tetrahydrocarbazole, 3-amino-6-N-[2-(4-nitrophenyl)ethyl]carboxamido-1,2,3,4-tetrahydrocarbazole, 3-amino-6-N-[2-(4-aminophenyl)ethyl]carboxamido-1,2,3,4-tetrahydrocarbazole, 3-amino-6-N-[2-(4-N-methylsulphonamidophenyl)ethyl]carboxamido-1,2,3,4-tetrahydrocarbazole, 3-amino-6-N-[2-(4-methoxyphenyl)ethyl]carboxamido-1,2,3,4-tetrahydrocarbazole, 3-amino-6-N-[2-(4-phenylsulphonamido)ethyl]carboxamido-1,2,3,4-tetrahydrocarbazole, 3-amino-6-N-[2-(4-chlorophenyl)ethyl]carboxamido-1,2,3,4-tetrahydrocarbazole, 3-amino-6-[E-3-(4-nitrophenyl)prop-2-enyl]carboxamido-1,2,3,4-tetrahydrocarbazole, 3-amino-6-[E-3-(4-bromophenyl)prop-2-enyl]carboxamido-1,2,3,4-tetrahydrocarbazole, 3-amino-6-[E-3-(4-methoxyphenyl)prop-2-enyl]carboxamido-1,2,3,4-tetrahydrocarbazole, 3-amino-6-[E-3-(3-methoxyphenyl)prop-2-enyl]carboxamido-1,2,3,4-tetrahydrocarbazole, 3-Amino-6-(E-3-(phenylprop-2-enyl)carboxamido-1,2,3,4-tetrahydrocarbazole, 3-amino-6-[E-3-(4-phenylsulphonamido)prop-2-enyl]carboxamido-1,2,3,4-tetrahydrocarbazole, 3-amino-6-[3-(4-methoxyphenyl)propyl]carboxamido-1,2,3,4-tetrahydrocarbazole, 3-amino-6-[E-3 (3-nitrophenyl)prop-2-enyl]carboxamido-1,2,3,4-tetrahydrocarbazole, 3-amino-6-[3-(3-methoxyphenyl)propyl]carboxamido-1,2,3,4-tetrahydrocarbazole, and salts thereof.

In a further aspect, the present invention also provides a process for the preparation of compounds of formula (I).

Compounds of formula (I) may be prepared for example by methods known in the art for the preparation of tetrahydrocarbazoles, such as:

A) Reaction of a compound of formula (II):

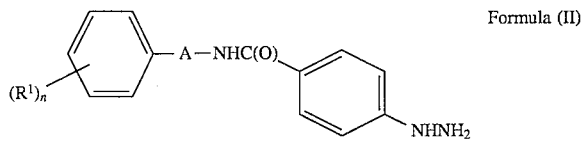

Formula (II)

(wherein $R^1$, A and n are as hereinbefore defined) or an acid addition salt thereof with a compound of formula (III):

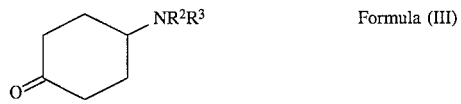

Formula (III)

(wherein $R^2$ and $R^3$ are as hereinbefore defined) or an N-protected derivative thereof; or B) Reaction of a compound of formula (IV):

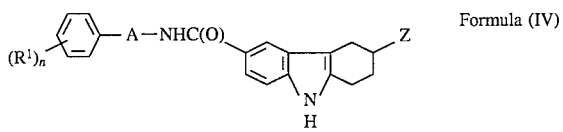

Formula (IV)

(wherein $R^1$, A and n are as defined for formula (I) and Z is a leaving group) with a compound of formula $HNR^2R^3$;

C) Reacting a compound of formula (V):

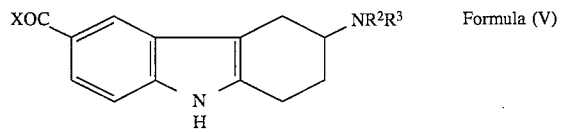

Formula (V)

wherein $R^2$ and $R^3$ are as hereinbefore defined and X is OH or a leaving group forming an activated carboxylic acid group —COX, with a compound of formula (VI):

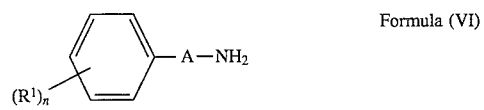

Formula (VI)

wherein $R^1$, A and n are as hereinbefore defined;

D) Conversion of one compound of formula (I) into another compound of formula (I) for example:

(i) to prepare a compound of formula (I) wherein one of $R^2$ and $R^3$ is hydrogen and the other is $C_{1-6}$alkyl, alkylation of a compound (I) in which $R^2$ and $R^3$ are both hydrogen; or (ii) to prepare a compound of formula (I) wherein A is $C_{3-5}$alkylene, reduction of a compound (I) wherein A is $C_{3-5}$alkenylene;

followed if necessary by deprotection of any protected nitrogen atoms and if desired by salt formation.

Process (A), which is a form of the Fischer Indole Synthesis, may be carried out using methods well known in the art. Thus, the reaction may be effected in a solvent, for example an alcohol such as ethanol or butanol; or acetic acid, and at a temperature in the range 0° to 150° C.

Hydrazines of formula (II), which are usually employed as the hydrochloride salt, are known compounds, or may be prepared by conventional methods, for example by an analogous method to process (C), by reaction of an amine of formula (VI), with a hydrazine of formula (VII):

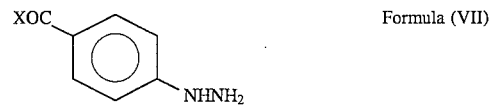

Formula (VII)

wherein X is as defined above.

A cyclohexanone of formula (III) may be prepared by oxidation of the corresponding cyclic alcohol, using an oxidising agent such as pyridinium chlorochromate, pyridinium dichromate, dipyridine Cr (VI) oxide, sodium hypochlorite, calcium hypochlorite or manganese dioxide.

The leaving group Z in the compounds of formula (IV) may be for example a halogen atom, or a sulphonyloxy group eg. p-toluenesulphonyloxy or methanesulphonyloxy. Process (B) may be effected in an inert organic solvent, such as an alcohol eg. methanol or an ether eg. tetrahydrofuran and at a temperature in the range 0° to 150° C. Compounds of formula (IV) may be obtained by reacting a hydrazine of formula (II) with an appropriately substituted cyclohexanone compound. When Z is acyloxy or sulphonyloxy this may be prepared from a compound (IV) wherein Z is hydroxy, using standard procedures.

Process (C) may be carried out according to standard methods for forming an amide bond. When X is a leaving group a compound of formula (V) represents an activated carboxylic acid derivative, such as an acid halide e.g. an acid chloride; or an ester e.g. methyl. Conditions for reaction with an amine (VI) will depend upon the particular type of activated derivative (V) employed.

When X is OH the carboxylic acid of formula (V) may be reacted with an amine (VI) in the presence of a coupling agent such as diphenylphosphorylazide, carbonyldiimidazole or dicyclohexylcarbodiimide.

Compounds of formula (V) may be prepared for example by reaction of a hydrazine of formula (VII) with a cyclohexanone of formula (III) or an N-protected derivative thereof in an analogous manner to process (A).

Alkylation according to process (D) may be effected by reacting an amine of formula (I) with an acylating agent, for example an anhydride, such as acetic or propionic anhydride, to form an intermediate in which one of $R^2$ or $R^3$ is —C(O)$C_{1-5}$alkyl, or —CHO followed by reduction of said intermediate to give the desired product. Alternatively an amine of formula (I) may be reacted with an aldehyde in the presence of a reducing agent such as sodium borohydride or sodium cyanoborohydride. Other reagents and conditions will be apparent to those skilled in the art.

Reduction of a compound (I) wherein A is alkenylene may be effected using hydrogen in the presence of a suitable catalyst such as palladium on charcoal or Raney nickel, in a solvent such as ethanol.

It will be appreciated that in many of the above reactions it will be necessary to protect the group —$NR^2R^3$ when one or both of the groups $R^2$ and $R^3$ represent hydrogen. Suitable N-protecting groups are well-known in the art and include for example acyl groups such as acetyl, trifluoroacetyl, benzoyl, or phthaloyl; alkoxy- or aralkoxycarbonyl groups such as methoxycarbonyl, t-butoxycarbonyl, or benzyloxycarbonyl; and aralkyl groups such as benzyl, diphenylmethyl or triphenylmethyl. When $R^2$ and $R^3$ both represent hydrogen the nitrogen atom is preferably protected as the phthalimide. The protecting groups should be easily removable at the end of the reaction sequence. N-deprotection may be effected by conventional methods, for example a phthaloyl group may be removed by reaction with hydrazine; an acyl group such as benzoyl may be cleaved by hydrolysis and an aralkyl group such as benzyl or an aralkoxycarbonyl group such as benzyloxycarbonyl may be cleaved by hydrogenolysis.

When a compound of formula (I) is obtained as a mixture of enantiomers these may be separated by conventional methods, for example by reaction of the mixture with a suitable optically active acid such as d-tartaric acid, 1-malic acid, 1-mandelic acid, 1-gulonic acid or 2,3:4,6-di-O-isopropylidene-keto-L-gulonic acid to give two diastereoisomeric salts which may be separated eg. by crystallisation. Alternatively mixtures of enantiomers may be separated by chromatography, for example on a chiral HPLC column.

Compounds of formula (I) have affinity for the 5-HT$_1$-like receptor and are expected to be useful in treating disease states which require modulation of the 5-HT$_1$-like receptor. In particular the compounds are 5-HT$_1$-like agonists (or partial agonists) and as such are expected to have utility in medicine in the treatment and/or prophylaxis of migraine, with and without aura and other conditions associated with cephalic pain, such as cluster headache, tension headache, headache associated with vascular disorders and trigeminal neuralgias.

In a further aspect, the invention provides a method of treatment of conditions which require modulation of the 5-HT$_1$-like receptor in particular migraine which comprises administering to a subject in need thereof an effective amount of a compound of formula (I) or a physiologically acceptable salt, solvate or hydrate thereof.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

BIOLOGICAL TEST METHODS

Rabbit Basilar Artery

Experiments were performed in intracranial arteries from rabbit isolated basilar artery in a similar method to one described previously (Parsons and Whalley, 1989. Eur J Pharmacol 174, 189–196.).

In brief, rabbits were killed by overdose with anaesthetic (sodium pentobarbitone). The whole brain was quickly removed and immersed in ice cold modified Kreb's solution and the basilar artery removed with the aid of a dissecting microscope. The Krebs solution was of the following composition (mM) $Na^+$ (120); $K^+$ (5); $Ca^{2+}$ (2.25); $Mg^{2+}$ (0.5); $Cl^-$ (98.5); $SO_4^{2-}$ (1); EDTA (0.04), equilibrated with 95% $O_2$/5% $CO_2$. The endothelium was removed by a gentle rubbing of the lumen with a fine metal wire. Arteries were then cut into ring segments (ca 4–5 mm wide) and set up for recording of isometric tension in 50 ml tissue baths in modified Krebs solution with the additional supplement of (mM); $Na^{2+}$ (20); fumarate (10); pyruvate (5); L-glutamate (5) and glucose (10). The arteries were then placed under a resting force of 3–4 mN maintained at 37° C. and the solution bubbled with 95% $O_2$/5% $CO_2$.

After tests for initial reactivity with 90 mM KCl depolarising solution and for lack of acetylcholine-induced relaxation of 5-HT (10 mM) precontraction, cumulative concentration-effect curves (2 nM–60 mM) to 5-HT were constructed in the presence of ascorbate 200 mM, cocaine 6 mM, indomethacin 2.8 mM, ketanserin 1 mM and prazosin 1 mM.

Following a 45–60 min wash period, cumulative concentration-effect curves to the test compounds or 5-HT (as a time match control) were constructed in the presence of ascorbate, indomethacin, cocaine, ketanserin and prazosin.

In this screen compounds of Examples 1, 3, 5, 6, 7, 8, 9, 13, 14, 15, 17 and 18 had $EC_{50}$ values between 0.09 and 4.01 μM.

The invention is further illustrated by the following non limiting examples.

EXAMPLE 1

3-Amino-6-N-(3-phenylpropyl)carboxamido-1,2,3,4-tetrahydrocarbazole oxalate salt (a) A mixture of 4-phthalimidocyclohexanone (2.43 g) and 4-hydrazinobenzoic acid (1.52 g) were combined in acetic acid and boiled for 12 hours. The precipitate was filtered and washed with acetic acid (3×10 ml) and diethyl ether (3×10 ml) to give 6-carboxy-3-phthalimido-1,2,3,4-tetrahydrocarbazole (1.50 g) m.p. 345°–348° C.

(b-i) To a solution of 6-carboxy-3-phthalimido-1,2,3,4-tetrahydrocarbazole (0.5 g), 3-phenylpropylamine (0.21 g) and triethylamine (0.29 g) in dimethylformamide (25 ml), diphenylphosphoryl azide (0.42 g) was added dropwise over 5 minutes. The reaction was stirred for 15 hours diluted with ethyl acetate (100 ml) and washed with water (3×50 ml). The organic phase was dried ($MgSO_4$), solvent removed at reduced pressure to give -6-N-(3-phenylpropyl)-3-phthalimido-carboxamido-1,2,3,4-tetrahydrocarbazole (0.65 g).

(b-ii) 6-N-(3-Phenylpropyl)-3-phthalimido-carboxamido-1,2,3,4-tetrahydrocarbazole (0.65 g) was dissolved in ethanol (10 ml) containing hydrazine hydrate (5.36 ml). After stirring at room temperature for 1 hour solvent was removed at reduced pressure and the residue column chromatographed (silica gel, dichloromethane/10% ammonia in methanol 0→5%). Appropriate fractions were combined solvent removed at reduced pressure and the obtained oil (0.32 g) treated with oxalic acid dihydrate (0.13 g) in methanol to give the title oxalate salt (0.31 g) m.p. 155°–157° C.

EXAMPLE 2

3-Amino-6-N-(4-phenylbutyl)carboxamido-1,2,3,4-tetrahydrocarbazole oxalate salt Using 6-carboxy-3-phthalimido-1,2,3,4-tetrahydrocarbazole (0.7 g) and 4-phenylbutylamine (0.32 g) instead of 3-phenylpropylamine in the method of Example 1(b) followed by recrystallisation from methanol gave the title compound (0.35 g) m.p. 138°–140° C.

EXAMPLE 3

3-Amino-6-N-(2-phenylethyl)carboxamido-1,2,3,4-tetrahydrocarbazole

Using 6-carboxy-3-phthalimido-1,2,3,4-tetrahydrocarbazole (0.7 g) and 4-phenylethylamine (0.26 g) instead of 3-phenylpropylamine in the method of Example 1(b) gave the title compound (0.33 g) m.p. 127°–130° C.

EXAMPLE 4

3-Amino-6-N-(phenylmethyl)carboxamido-1,2,3,4-tetrahydrocarbazole oxalate salt Using 6-carboxy-3-phthalimido-1,2,3,4-tetrahydrocarbazole (0.50 g) and benzylamine (0.16 g) instead of 3-phenylpropylamine in the method of Example 1(b) followed by recrystallisation from methanol/diethyl ether gave the title compound (0.07 g) m.p. 160°–163° C.

EXAMPLE 5

3-Amino-6-N-[2-(4-nitrophenyl)ethyl]carboxamido-1,2,3,4-tetrahydrocarbazole fumarate salt (a) Using 6-carboxy-3-phthalimido-1,2,3,4-tetrahydrocarbazole (2.1 g), and 2-(4-nitrophenyl)ethylamine hydrochloride instead of 3-phenylpropylamine in the method of Example 1 (b-i) followed by column chromatography (silica gel, dichloromethane/10% ammonia in methanol 0→4%) gave 6-N-[2-(4-nitrophenyl)ethyl]carboxamido-3-phthalimido-1,2,3,4-tetrahydrocarbazole (0.62 g).

$^1$H NMR ($d_6$-DMSO) δ 2.10(m,1H), 2.62–2.82(m1H), 2.92(m,2H), 2.99(t,2H), 3.32(m,1H), 3.50–3.57(m,2H), 4.53(m,1H), 7.27(d,1H), 7.52(d,3H), 7.86–7.92(m,5H), 8.15(d,2H), 8.86(t,1H) and 11.08(s,1H).

(b) 6-N-[2-(4-Nitrophenyl)ethyl]carboxamido-3-phthalimido-1,2,3,4-tetrahydrocarbazole (0.5 g) was treated according to the method of Example 1 (b-ii) to give the free base of the title compound (0.07 g) m.p. 262°–264° C. The fumarate salt was prepared by recrystallisation of the title free base (0.17 g) with fumaric acid (0.08 g) from methanol/diethyl ether to give the title compound.

EXAMPLE 6

3-Amino-6-N-[2-(4-aminophenyl)ethyl]carboxamido-1,2,3,4-tetrahydrocarbazole oxalate salt (a-i) 6-N-[2-(4-Nitrophenyl)ethyl]carboxamido-3-phthalimido-1,2,3,4-tetrahydrocarbazole (0.47 g) in ethanol (30 ml) containing 10% palladium on charcoal (0.1 g) was shaken at room temperature under an atmosphere of hydrogen (44 psi) for 2 hours to give 6-N-[2-(4-aminophenyl)ethyl]carboxamido-3-phthalimido-1,2,3,4-tetrahydrocarbazole.

(a-ii) The reaction mixture was filtered (celite pad) and treated with hydrazine hydrate (1.96 g) according to the method of Example 1(b-ii) followed by conversion to the oxalate salt and recrystallisation from methanol to give the title compound (0.136 g) m.p. 248°–251° C.

EXAMPLE 7

3-Amino-6-N-[2-(4-methylsulphonamidophenyl)ethyl]carboxamido-1,2,3,4-tetrahydrocarbazole oxalate salt (a) To a solution of 3-amino-6-N-[2-(4-nitrophenyl)ethyl]carboxamido-1,2,3,4-tetrahydrocarbazole (0.206 g) in tetrahydrofuran (15 ml) di-tert-butyl pyrocarbonate (0.13 g) was added and the mixture stirred for 3 hours to give after removal of solvent 3-tert-butoxycarbonylamino-6-N-[2-(4-nitrophenyl)ethyl]carboxamido-1,2,3,4-tetrahydrocarbazole (0.28 g).

(b) Using the method of Example 6 (a-i), 3-tert-butoxycarbonylamino-6-N-[2-(4-nitrophenyl)ethyl]carboxamido-1,2,3,4-tetrahydrocarbazole (0.685 g) was reduced to 3-tert-butoxycarbonylamino-6-N-[2-(4-aminophenyl)ethyl]carboxamido-1,2,3,4-tetrahydrocarbazole (0.28 g).

$^1$H NMR (d$_6$-DMSO) δ 1.42(s,9H), 1.76(m,1H), 2.03(m,1H), 2.50(m,1H masked by dmso), 2.65(t,2H), 2.79(m,2H), 2.96(dd,1H), 3.38(m,2H masked by water), 3.74(m,1H), 4.85(br.s,2H), 6.49(d,2H), 6.89(d,2H), 7.03(d,1H), 7.24(d,1H), 7.53(d,1H), 7.90(s,1H), 8.29(t,1H) and 10.94(s,1H).

(c) A solution of 3-tert-butoxycarbonylamino-6-N-[2-(4-aminophenyl)ethyl]carboxamido-1,2,3,4-tetrahydrocarbazole (0.28 g), triethylamine (0.13 g) and methanesulphonyl chloride (0.08 g) in pyridine (10 ml) was heated at 60° C. for 5 hours. The mixture was diluted with water (20 ml) and toluene (20 ml), solvent removed at reduced pressure and the residue azeotroped with toluene (4×10 ml). The residue was chromatographed (silica gel, dichloromethane/10% ammonia in methanol 0→2.5% eluant) to give 3-tert-butoxycarbonylamino-6-N-[2-(4-methanesulphonamidophenyl)ethyl]carboxamido-1,2,3,4-tetrahydrocarbazole (0.216 g).

(d) A suspension of 3-tert-butoxycarbonylamino-6-N-[2-(4-methanesulphonamidophenyl)ethyl]carboxamido-1,2,3,4-tetrahydrocarbazole (0.216 g) in a mixture of acetic acid (4.4 ml) and 2N hydrochloric acid (1.2 ml) was stirred for 16 hour. Solvent was removed at reduced pressure and the residue chromatographed (silica gel, dichloromethane/10% ammonia in methanol 0→14% eluant) to give, after formation of the oxalate salt and recrystallisation from methanol the title compound (0.08 g) m.p. 270°–273° C.

EXAMPLE 8

3-Amino-6-N-[2-(4-methoxyphenyl)ethyl]carboxamido-1,2,3,4-tetrahydrocarbazole oxalate salt Using 6-carboxy-3-phthalimido-1,2,3,4-tetrahydrocarbazole (0.7 g) and 2-(4-methoxyphenyl)ethylamine (0.32 g) instead of 3-phenylpropylamine in the method of Example 1(b) followed by recrystallisation from methanol/diethyl ether gave the title compound (0.10 g) m.p. 147°–150° C.

EXAMPLE 9

3-Amino-6-N-[2-(4-phenylsulphonamido)ethyl]carboxamido-1,2,3,4-tetrahydrocarbazole Using 6-carboxy-3-phthalimido-1,2,3,4-tetrahydrocarbazole (0.7 g) and 2-(4-phenylsulphonamido)ethylamine (0.43 g) instead of 3-phenylpropylamine in the method of Example 1(b) followed by column chromatography (silica gel, dichloromethane/10% ammonia in methanol 0→20% eluant), gave the title compound (0.04 g) m.p. 219° C.

EXAMPLE 10

3-Amino-6-N-[2-(4-chlorophenyl)ethyl]carboxamido-1,2,3,4-tetrahydrocarbazole oxalate salt Using 6-carboxy-3-phthalimido-1,2,3,4-tetrahydrocarbazole (0.7 g) and 2-(4-chlorophenyl)ethylamine (0.30 g) instead of 3-phenylpropylamine in the method of Example 1(b) followd by recrystallisation from methanol gave the title compound (0.04 g) m.p. 158° C.

EXAMPLE 11

3-Amino-6-[E-3-(4-nitrophenyl)prop-2-enyl]carboxamido-1,2,3,4-tetrahydrocarbazole oxalate salt Using 6-carboxy-3-phthalimido-1,2,3,4-tetrahydrocarbazole (0.60 g) and 3-(4-nitrophenyl)prop-2-enyl amine (0.32 g) (N. J. Malek and A. E. Moorman J. Org. Chem. 1982, 47, 5395) instead of 3-phenylpropylamine in the method of Example 1(b) gave, after recrystallisation from methanol/diethyl ether, the title compound (0.045 g) m.p. 139°–141° C. M/Z: $C_{22}H_{22}N_4O_3$=391 (M+1)$^+$.

EXAMPLE 12

3-Amino-6-[E-3-(4-bromophenyl)prop-2-enyl]carboxamido-1,2,3,4-tetrahydrocarbazole oxalate salt The title compound was prepared according to the method of Example 1(b) from 6-carboxy-3-phthalimido-1,2,3,4-tetrahydrocarbazole (1.0 g) using 3-(4-bromophenyl)prop-2-enyl amine (0.59 g) (N. J. Malek and A. E. Moorman J. Org. Chem. 1982, 47, 5395) instead of 3-phenylpropylamine. This product (1.04 g) was purified by preparing from it 3-tert-butoxycarbonylamino-6-[E-3-(4-bromophenyl)prop-2-enyl]carboxamido-1,2,3,4-tetrahydrocarbazole (0.60 g) according to the method of Example 7(a) and subsequent treatment with methanol/3N hydrochloric acid at room temperature for 16 hours. Solvent was removed at reduced pressure and the residue columned. The resulting product was converted to the oxalate salt and recrystallised from methanol/ether to give the title compound (0.03 g) m.p. 210° C. m/z: $C_{22}H_{22}BrNO_3$=424/426 (M+1)$^+$.

EXAMPLE 13

3-Amino-6-[E-3-(4-methoxyphenyl)prop-2-enyl]carboxamido-1,2,3,4-tetrahydrocarbazole oxalate salt Using 6-carboxy-3-phthalimido-1,2,3,4-tetrahydrocarbazole (0.70 g) and E-3-(4-methoxyphenyl)prop-2-enyl amine (0.33 g) instead of 3-phenylpropylamine. in the method of Example 1(b) followed by recrystallisation from methanol/diethyl ether gave the title compound (0.42 g) m.p. 145°–147° C. m/z: $C_{23}H_{25}N_3O_2=376$ (M+1)$^+$.

EXAMPLE 14

3-Amino-6-[E-3-(3-methoxyphenyl)prop-2-enyl]carboxamido-1,2,3,4-tetrahydrocarbazole oxalate salt Using 6-carboxy-3-phthalimido-1,2,3,4-tetrahydrocarbazole (1.0 g) and E-3-(3-methoxyphenyl)prop-2-enyl amine (0.50 g) instead of 3-phenylpropylamine in the method of Example 1(b) followed by recrystallisation from methanol/diethyl ether gave the title compound (0.42 g) m.p. 148°→210° C. (decomp).

1H NMR (d6-DMSO)δ 1.9(m,1H), 2.2(m,1H), 2.9(m,3H), 3.1(m,1H), 3.4(m,1H), 3.8(s,3H), 4.1(t,2H), 6.4(dt,1H), 6.5(d,1H), 6.8(d,1H), 7.0(d+s,2H), 7.2(t,1H), 7.3(d,1H), 7.6(d,1H), 8.0(s,1H), 8.6(t,1H) and 11.1(br.s,1H). m/z: $C_{23}H_{25}N_3O_2=375$ (M$^+$).

EXAMPLE 15

3-Amino-6-(E-3-(phenylprop-2-enyl)carboxamido-1,2,3,4-tetrahydrocarbazole oxalate salt Using 6-carboxy-3-phthalimido-1,2,3,4-tetrahydrocarbazole (0.50 g) and E-3-phenylprop-2-enyl amine (0.21 g) (N. J. Malek and A. E. Moorman J. Org. Chem. 1982, 47, 5395) instead of 3-phenylpropylamine in the method of Example 1(b) followed by recrystallisation from methanol/diethyl ether gave the title compound (0.053 g) m.p. 185°–203° C.

$^1$H NMR (d$_6$ DMSO) δ 1.9(m,1H), 2.2(m,1H), 2.7(m,1H), 2.9(m,2H), 3.1(m,1H), 4.1(t,2H), 6.3(dt,1H), 6.5(d,1H), 7.4–7.4(m,6H), 7.6(d,1H), 8.0(s,1H), 8.6t,1H) and 11.1(br.s, 1H). m/z: $C_{22}H_{23}N_3O=345$ (M$^+$).

EXAMPLE 16

3-Amino-6-[E-3-(4-phenylsulphonamido)prop-2-enyl]carboxamido-1,2,3,4-tetrahydrocarbazole oxalate salt Using 6-carboxy-3-phthalimido-1,2,3,4-tetrahydrocarbazole (0.37 g) and E-3-(4-phenylsulphonamido)prop-2-enyl amine (0.19 g) instead of 3-phenylpropylamine in the method of Example 1(b) followed by recrystallisation from methanol/diethyl ether gave the title compound (0.047 g) m.p. 285°–287° C. m/z: $C_{22}H_{24}N_4O_3S=425$ (M+1 )$^+$.

EXAMPLE 17

3-Amino-6-[3-(4-methoxyphenyl)propyl]carboxamido-1,2,3,4-tetrahydrocarbazole oxalate salt A solution of 3-amino-6-[E-3-(4-methoxyphenyl)prop-2-enyl]carboxamido-1,2,3,4-tetrahydrocarbazole (0.15 g) in ethanol (40 ml) was shaken with 10% Pd/C (0.05 g) under an atmosphere of hydrogen (45 psi) at room temperature for 2 hours. The solution was filtered (celite pad), solvent removed at reduced pressure and the residue converted to the oxalate salt to give the title compound (0.045 g) m.p. 155°–200° C. (decomp).

$^1$H NMR (d$_6$-DMSO)δ 1.8(m,2H), 1.9(m,1H), 2.2(m,1H), 2.6(t,2H), 2.7(m,1H), 2.8(m,2H), 3.1(m,1H), 3.3(m,2H), 3.4(m,1H), 3.7(s,3H), 6.8(d,2H), 7.1(d,2H), 7.3(d,1H), 7.6(d,1H), 8.0(s,1H), 8.3(t,1H), 11.1(br.s,1H). m/z: $C_{23}H_{27}N_3O_2=377$ (M$^+$).

EXAMPLE 18

3-Amino-6-[E-3 (3-nitrophenyl)prop-2-enyl]carboxamido-1,2,3,4-tetrahydrocarbazole oxalate salt Using 6-carboxy-3-phthalimido-1,2,3,4-tetrahydrocarbazole (1.0 g) and E-3-(3-nitrophenyl)prop-2-enylamine (0.50 g) instead of E-3-(4-bromophenyl)prop-2-enylamine in the method of Example 12, followed by recrystallisation from methanol/ether gave the title compound m.p. 165°–175° C. m/z: $C_{22}H_{22}N_4O_3=391$ (M+1)$^+$.

EXAMPLE 19

3-Amino-6-[3-(3-methoxyphenyl)propyl]carboxamido-1,2,3,4-tetrahydrocarbazole oxalate salt A solution of 3-amino-6-[E-3-(3-methoxyphenyl)prop-2-enyl]carboxamido-1,2,3,4-tetrahydrocarbazole (0.12 g) in ethanol (40 ml) was shaken with 10% Pd/C (0.05 g) under an atmosphere of hydrogen (45 psi) at room temperature for 2 hours. The solution was filtered (celite pad), solvent removed at reduced pressure and the residue converted to the oxalate salt to give the title compound (0.055 g) m.p. softens 120–135 melts 200°–205° C.

$^1$H NMR (d$_6$-DMSO)δ 1.8(m,2H), 1.9(m,1H), 2.2(m1H), 2.6(t,2H), 2.7(m,1H), 2.9(m,2H), 3.1(m,1H), 3.3(m,2H), 3.5(m,2H), 3.5(m,1H), 3.7(s,3H), 6.7(d,1H), 6.8(d and s,2H), 7.2(t,1H), 7.3(d,1H), 7.6(d,1H), 7.9(s,1H), 8,3(t,1H) and 11.1(s,1H). m/z: $C_{23}H_{27}N_3O_2=378$ (M+1)$^+$.

We claim:

1. A compound of formula (I):

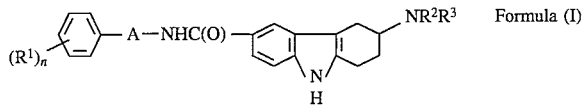

wherein

R$^1$ represents halogen, $C_{1-4}$alkyl, $C_{1-4}$alkoxy, hydroxy, NO$_2$, —NR$^4$R$^5$, R$^4$R$^5$NCO(CH$^2$)$_m$—, R$^4$R$^5$NSO$_2$(CH$_2$)$_m$—, R$^6$CONH(CH$_2$)$_m$— or R$^7$SO$_2$NH(CH$_2$)$_m$—;

R$^4$ and R$^5$ each independently represent hydrogen or $C_{1-4}$alkyl or NR$^4$R$^5$ represents a 5- to 7-membered heterocyclic ring;

R$^6$ represents hydrogen or $C_{1-4}$alkyl;

R$^7$ represents $C_{1-4}$alkyl;

m is zero, 1 or 2;

n is zero or 1 to 5;

R$^2$ and R$^3$ each independently represent hydrogen, $C_{1-6}$alkyl or benzyl or —NR$^2$R$^3$ represents a pyrrolidino, piperidino or hexahydroazepino ring; and A represents a bond, a $C_{1-5}$alkylene chain or a $C_{3-5}$alkenylene chain wherein the double bond is not adjacent the nitrogen atom;

or a salt thereof.

2. A compound according to claim 1 wherein A represents a $C_{1-4}$alkylene chain or a $C_{3-4}$alkenylene chain.

3. A compound according to claim 2 wherein A represents —(CH$_2$)$_2$—, —(CH$_2$)$_3$— or —CH=CHCH$_2$—.

4. A compound according to claim 1 wherein n is from zero to 3.

5. A compound according to claim 1 wherein $R^1$ represents halogen, $C_{1-4}$alkoxy, $NO_2$, $-NR^4R^5$, $R^4R^5NSO_2(CH_2)_m-$, or $R^7SO_2NH(CH_2)_m-$ where $R^4, R^5, R^7$ and m are as defined above.

6. A compound according to claim 1 wherein $R^2$ and $R^3$ independently represent hydrogen, methyl or ethyl.

7. A compound of formula (I) selected from:

3-amino-6-N-(3-phenylpropyl)carboxamido-1,2,3,4-tetrahydrocarbazole, 3-amino-6-N-(4-phenylbutyl)carboxamido-1,2,3,4-tetrahydrocarbazole, 3-amino-6-N-(2-phenylethyl)carboxamido-1,2,3,4-tetrahydrocarbazole, 3-amino-6-N-(benzylmethyl)carboxamido-1,2,3,4-tetrahydrocarbazole, 3-amino-6-N-[2-(4-nitrophenyl)ethyl]carboxamido-1,2,3,4-tetrahydrocarbazole, 3-amino-6-N-[2-(4-aminophenyl)ethyl]carboxamido-1,2,3,4-tetrahydrocarbazole, 3-amino-6-N-[2-(4-methylsulphonamidophenyl)ethyl]carboxamido-1,2,3,4-tetrahydrocarbazole, 3-amino-6-N-[2-(4-N-methoxyphenyl)ethyl]carboxamido-1,2,3,4-tetrahydrocarbazole, 3-amino-6-N-[2-(4-phenylsulphonamido)ethyl]carboxamido-1,2,3,4-tetrahydrocarbazole, 3-amino-6-N-[2-(4-chlorophenyl)ethyl]carboxamido-1,2,3,4-tetrahydrocarbazole, 3-amino-6-[E-3-(4-nitrophenyl)prop-2-enyl]carboxamido-1,2,3,4-tetrahydrocarbazole, 3-amino-6-[E-3-(4-bromophenyl)prop-2-enyl]carboxamido-1,2,3,4-tetrahydrocarbazole, 3-amino-6-[E-3-(4-methoxyphenyl)prop-2-enyl]carboxamido-1,2,3,4-tetrahydrocarbazole, 3-amino-6-[E-3-(3-methoxyphenyl)prop-2-enyl]carboxamido-1,2,3,4-tetrahydrocarbazole, 3-amino-6-(E-3-(phenylprop-2-enyl)carboxamido-1,2,3,4-tetrahydrocarbazole, 3-amino-6-[E-3-(4-phenylsulphonamido)prop-2-enyl]carboxamido-1,2,3,4-tetrahydrocarbazole, 3-amino-6-[3-(4-methoxyphenyl)propyl]carboxamido-1,2,3,4-tetrahydrocarbazole, 3-amino-6-[E-3(3-nitrophenyl)prop-2-enyl]carboxamido-1,2,3,4-tetrahydrocarbazole, 3-amino-6-[3-(3-methoxyphenyl)propyl]carboxamido-1,2,3,4-tetrahydrocarbazole, or a salt thereof.

8. A method of treatment of a condition which requires modulation of the 5-$HT_1$-like receptor which comprises administering to a subject in need thereof an effective amount of a compound of formula (I) as claimed in claim 1 or a physiologically acceptable salt, solvate or hydrate thereof.

9. A pharmaceutical composition comprising a compound of formula (I) as claimed in claim 1 or a physiologically acceptable salt, solvate or hydrate thereof and a physiologically acceptable carrier.

* * * * *